United States Patent
Kolafa et al.

(10) Patent No.: US 7,962,220 B2
(45) Date of Patent: Jun. 14, 2011

(54) COMPENSATION REDUCTION IN TISSUE STIMULATION THERAPY

(75) Inventors: Jerry J. Kolafa, Richmond, TX (US); Steven E. Maschino, Seabrook, TX (US)

(73) Assignee: Cyberonics, Inc.

( * ) Notice: Subject to any disclaimer, the term of this patent is extended or adjusted under 35 U.S.C. 154(b) by 1132 days.

(21) Appl. No.: 11/414,391

(22) Filed: Apr. 28, 2006

(65) Prior Publication Data

US 2007/0255374 A1 Nov. 1, 2007

(51) Int. Cl.
*A61N 1/05* (2006.01)
(52) U.S. Cl. .......................................... 607/46
(58) Field of Classification Search .............. 607/46, 607/45, 2, 40, 58
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |

(Continued)

FOREIGN PATENT DOCUMENTS

CA 2339971 6/2004

(Continued)

OTHER PUBLICATIONS

Lockard et al., "Feasibility and Safety of Vagal Stimulation in Monkey Model;" Epilepsia, vol. 31 (Supp. 2) (1990), pp. S20-S26.

(Continued)

*Primary Examiner* — Carl H. Layno
*Assistant Examiner* — Jon-Eric C. Morales
(74) *Attorney, Agent, or Firm* — Conley Rose PC; Jonathan D. Rowell; Darrell N. Fuller

(57) ABSTRACT

Methods and systems for reducing compensation of the body to therapy delivered by an implanted medical device are described herein. The disclosed techniques cause a change from one therapy protocol to another therapy protocol based on the occurrence of an event (e.g., time, user activations of a sensor, input from a physiological sensor, etc.). The therapy protocols of the implanted medical device differ in terms of the on-time and off-time, but effectuate the same or similar duty cycle.

18 Claims, 4 Drawing Sheets

U.S. PATENT DOCUMENTS

| | | | |
|---|---|---|---|
| 4,977,985 A | 12/1990 | Wells et al. | |
| 5,025,807 A | 6/1991 | Zabara | |
| 5,081,987 A | 1/1992 | Nigam | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,205,285 A | 4/1993 | Baker, Jr. | |
| 5,215,086 A | 6/1993 | Terry, Jr. et al. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,330,507 A | 7/1994 | Schwartz | |
| 5,330,515 A * | 7/1994 | Rutecki et al. | 607/46 |
| 5,334,221 A | 8/1994 | Bardy | |
| 5,354,320 A | 10/1994 | Schaldach et al. | |
| 5,411,531 A | 5/1995 | Hill et al. | |
| 5,411,540 A | 5/1995 | Edell et al. | |
| 5,423,872 A | 6/1995 | Cigaina | |
| 5,507,784 A | 4/1996 | Hill et al. | |
| 5,522,862 A | 6/1996 | Testerman et al. | |
| 5,522,865 A | 6/1996 | Schulman et al. | |
| 5,540,730 A | 7/1996 | Terry, Jr. et al. | |
| 5,540,734 A | 7/1996 | Zabara | |
| 5,571,150 A | 11/1996 | Wernicke et al. | |
| 5,601,617 A | 2/1997 | Loeb et al. | |
| 5,611,350 A | 3/1997 | John | |
| 5,645,570 A | 7/1997 | Corbucci | |
| 5,651,378 A | 7/1997 | Matheny et al. | |
| 5,658,318 A | 8/1997 | Stroetmann et al. | |
| 5,690,681 A | 11/1997 | Geddes et al. | |
| 5,690,688 A | 11/1997 | Noren et al. | |
| 5,690,691 A | 11/1997 | Chen et al. | |
| 5,700,282 A | 12/1997 | Zabara | |
| 5,702,428 A | 12/1997 | Tippey et al. | |
| 5,702,429 A | 12/1997 | King | |
| 5,707,400 A | 1/1998 | Terry, Jr. et al. | |
| 5,755,750 A | 5/1998 | Petruska et al. | |
| 5,792,212 A | 8/1998 | Weijand | |
| 5,800,474 A | 9/1998 | Benabid et al. | |
| 5,814,092 A | 9/1998 | King | |
| 5,836,994 A | 11/1998 | Bourgeois | |
| 5,861,014 A | 1/1999 | Familoni | |
| 5,913,882 A | 6/1999 | King | |
| 5,916,239 A | 6/1999 | Geddes et al. | |
| 5,928,272 A | 7/1999 | Adkins et al. | |
| 5,941,906 A | 8/1999 | Barreras, Sr. et al. | |
| 5,995,868 A | 11/1999 | Dorfmeister et al. | |
| 6,002,966 A | 12/1999 | Loeb et al. | |
| 6,016,449 A | 1/2000 | Fischell et al. | |
| 6,041,258 A | 3/2000 | Cigaina et al. | |
| 6,083,249 A | 7/2000 | Familoni | |
| 6,101,412 A | 8/2000 | Duhaylongsod | |
| 6,104,955 A | 8/2000 | Bourgeois | |
| 6,104,956 A | 8/2000 | Naritoku et al. | |
| 6,115,628 A | 9/2000 | Stadler et al. | |
| 6,132,361 A | 10/2000 | Epstein et al. | |
| 6,141,590 A | 10/2000 | Renirie et al. | |
| 6,161,044 A | 12/2000 | Silverstone | |
| 6,167,311 A | 12/2000 | Rezai | |
| 6,175,764 B1 | 1/2001 | Loeb et al. | |
| 6,188,929 B1 | 2/2001 | Giordano | |
| 6,219,580 B1 | 4/2001 | Faltys et al. | |
| 6,221,908 B1 | 4/2001 | Kilgard et al. | |
| 6,238,423 B1 | 5/2001 | Bardy | |
| 6,249,704 B1 | 6/2001 | Maltan et al. | |
| 6,253,109 B1 | 6/2001 | Gielen | |
| 6,266,564 B1 | 7/2001 | Hill et al. | |
| 6,269,270 B1 | 7/2001 | Boveja | |
| 6,295,472 B1 | 9/2001 | Rubinstein et al. | |
| 6,304,775 B1 | 10/2001 | Iasemidis et al. | |
| 6,308,102 B1 | 10/2001 | Sieracki et al. | |
| 6,324,421 B1 | 11/2001 | Stadler et al. | |
| 6,327,503 B1 | 12/2001 | Familoni | |
| 6,339,725 B1 | 1/2002 | Naritoku et al. | |
| 6,341,236 B1 | 1/2002 | Osorio et al. | |
| 6,353,762 B1 | 3/2002 | Baudino et al. | |
| 6,356,788 B2 | 3/2002 | Boveja | |
| 6,358,203 B2 | 3/2002 | Bardy | |
| 6,366,813 B1 | 4/2002 | DiLorenzo | |
| 6,366,814 B1 | 4/2002 | Boveja et al. | |
| 6,374,140 B1 | 4/2002 | Rise | |
| 6,381,493 B1 | 4/2002 | Stadler et al. | |
| 6,381,496 B1 | 4/2002 | Meadows et al. | |
| 6,381,499 B1 | 4/2002 | Taylor et al. | |
| 6,418,344 B1 | 7/2002 | Rezai et al. | |
| 6,425,852 B1 | 7/2002 | Epstein et al. | |
| 6,438,423 B1 | 8/2002 | Rezai et al. | |
| 6,449,512 B1 | 9/2002 | Boveja | |
| 6,453,199 B1 | 9/2002 | Kobozev | |
| 6,459,936 B2 | 10/2002 | Fischell et al. | |
| 6,463,328 B1 | 10/2002 | John | |
| 6,466,822 B1 | 10/2002 | Pless | |
| 6,473,639 B1 | 10/2002 | Fischell et al. | |
| 6,473,644 B1 | 10/2002 | Terry, Jr. et al. | |
| 6,477,417 B1 | 11/2002 | Levine | |
| 6,477,418 B2 | 11/2002 | Plicchi et al. | |
| 6,480,743 B1 | 11/2002 | Kirkpatrick et al. | |
| 6,484,132 B1 | 11/2002 | Hively et al. | |
| 6,487,446 B1 | 11/2002 | Hill et al. | |
| 6,505,074 B2 | 1/2003 | Boveja et al. | |
| 6,522,928 B2 | 2/2003 | Whitehurst et al. | |
| 6,532,388 B1 | 3/2003 | Hill et al. | |
| 6,549,804 B1 | 4/2003 | Osorio et al. | |
| 6,556,868 B2 | 4/2003 | Naritoku et al. | |
| 6,564,102 B1 | 5/2003 | Boveja | |
| 6,565,503 B2 | 5/2003 | Leysieffer et al. | |
| 6,579,280 B1 | 6/2003 | Kovach et al. | |
| 6,587,719 B1 | 7/2003 | Barrett et al. | |
| 6,587,724 B2 | 7/2003 | Mann | |
| 6,587,726 B2 | 7/2003 | Lurie et al. | |
| 6,587,727 B2 | 7/2003 | Osorio et al. | |
| 6,591,138 B1 | 7/2003 | Fischell et al. | |
| 6,594,524 B2 | 7/2003 | Esteller et al. | |
| 6,600,953 B2 | 7/2003 | Flesler et al. | |
| 6,609,025 B2 | 8/2003 | Barrett et al. | |
| 6,609,030 B1 | 8/2003 | Rezai et al. | |
| 6,609,031 B1 | 8/2003 | Law et al. | |
| 6,610,713 B2 | 8/2003 | Tracey | |
| 6,611,715 B1 | 8/2003 | Boveja | |
| 6,612,983 B1 | 9/2003 | Marchal | |
| 6,615,081 B1 | 9/2003 | Boveja | |
| 6,615,084 B1 | 9/2003 | Cigaina | |
| 6,615,085 B1 | 9/2003 | Boveja | |
| 6,622,038 B2 | 9/2003 | Barrett et al. | |
| 6,622,041 B2 | 9/2003 | Terry, Jr. et al. | |
| 6,622,047 B2 | 9/2003 | Barrett et al. | |
| 6,628,987 B1 | 9/2003 | Hill et al. | |
| 6,656,960 B2 | 12/2003 | Puskas | |
| 6,662,053 B2 | 12/2003 | Borkan | |
| 6,668,191 B1 | 12/2003 | Boveja | |
| 6,671,547 B2 | 12/2003 | Lyster et al. | |
| 6,671,555 B2 | 12/2003 | Gielen et al. | |
| 6,671,556 B2 | 12/2003 | Osorio et al. | |
| 6,684,104 B2 | 1/2004 | Gordon et al. | |
| 6,684,105 B2 | 1/2004 | Cohen et al. | |
| 6,690,973 B2 | 2/2004 | Hill et al. | |
| 6,690,974 B2 | 2/2004 | Archer et al. | |
| 6,708,064 B2 | 3/2004 | Rezai | |
| 6,721,603 B2 | 4/2004 | Zabara et al. | |
| 6,731,979 B2 | 5/2004 | MacDonald | |
| 6,731,986 B2 | 5/2004 | Mann | |
| 6,754,536 B2 | 6/2004 | Swoyer et al. | |
| 6,760,626 B1 | 7/2004 | Boveja | |
| 6,764,498 B2 | 7/2004 | Mische | |
| 6,768,969 B1 | 7/2004 | Nikitin et al. | |
| 6,775,573 B2 | 8/2004 | Schuler et al. | |
| 6,793,670 B2 | 9/2004 | Osorio et al. | |
| 6,819,956 B2 | 11/2004 | DiLorenzo | |
| 6,826,428 B1 | 11/2004 | Chen et al. | |
| 6,832,114 B1 | 12/2004 | Whitehurst et al. | |
| 6,853,862 B1 | 2/2005 | Marchal et al. | |
| 6,885,888 B2 | 4/2005 | Rezai | |
| 6,895,278 B1 | 5/2005 | Gordon | |

| | | |
|---|---|---|
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2005/0049649 A1* | 3/2005 | Luders et al. .......... 607/45 |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja et al. |
| 2006/0015153 A1* | 1/2006 | Gliner et al. .......... 607/45 |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | Dilorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259077 A1* | 11/2006 | Pardo et al. .......... 607/2 |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0027486 A1 | 2/2007 | Armstrong |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073346 A1 | 3/2007 | Corbucci |
| 2007/0073355 A1 | 3/2007 | Dilorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner |
| 2007/0123946 A1 | 5/2007 | Masoud |
| 2007/0135855 A1 | 6/2007 | Foshee et al. |
| 2007/0142862 A1 | 6/2007 | Dilorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | Dilorenzo et al. |
| 2007/0156179 A1 | 7/2007 | Karashurov |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |

| | | | |
|---|---|---|---|
| 2007/0250145 A1 | 10/2007 | Kraus et al. | |
| 2007/0255147 A1 | 11/2007 | Drew et al. | |
| 2007/0255155 A1 | 11/2007 | Drew et al. | |
| 2007/0255330 A1 | 11/2007 | Lee et al. | |
| 2007/0255337 A1 | 11/2007 | Lu | |
| 2007/0260147 A1 | 11/2007 | Giftakis et al. | |
| 2007/0260289 A1 | 11/2007 | Giftakis et al. | |
| 2007/0265489 A1 | 11/2007 | Fowler et al. | |
| 2007/0265508 A1 | 11/2007 | Sheikhzadeh-Nadjar et al. | |
| 2007/0265536 A1 | 11/2007 | Giftakis et al. | |
| 2007/0272260 A1 | 11/2007 | Nikitin et al. | |
| 2007/0282177 A1 | 12/2007 | Pilz | |
| 2007/0287931 A1 | 12/2007 | Dilorenzo | |
| 2007/0288072 A1 | 12/2007 | Pascual-Leone et al. | |
| 2007/0299349 A1 | 12/2007 | Alt et al. | |
| 2007/0299473 A1 | 12/2007 | Matos | |
| 2007/0299480 A1 | 12/2007 | Hill | |
| 2008/0015651 A1 | 1/2008 | Ettori et al. | |
| 2008/0015652 A1 | 1/2008 | Maile et al. | |
| 2008/0021332 A1 | 1/2008 | Brainard, III | |
| 2008/0021341 A1 | 1/2008 | Harris et al. | |
| 2008/0021517 A1 | 1/2008 | Dietrich | |
| 2008/0021520 A1 | 1/2008 | Dietrich | |
| 2008/0027347 A1 | 1/2008 | Harris et al. | |
| 2008/0027348 A1 | 1/2008 | Harris et al. | |
| 2008/0027515 A1 | 1/2008 | Harris et al. | |
| 2008/0033502 A1 | 2/2008 | Harris et al. | |
| 2008/0033503 A1 | 2/2008 | Fowler et al. | |
| 2008/0033508 A1 | 2/2008 | Frei et al. | |
| 2008/0039895 A1 | 2/2008 | Fowler et al. | |
| 2008/0046035 A1 | 2/2008 | Fowler et al. | |
| 2008/0046037 A1 | 2/2008 | Haubrich et al. | |
| 2008/0046038 A1 | 2/2008 | Hill et al. | |
| 2008/0051852 A1 | 2/2008 | Dietrich et al. | |
| 2008/0058884 A1 | 3/2008 | Matos | |
| 2008/0064934 A1 | 3/2008 | Frei et al. | |
| 2008/0071323 A1 | 3/2008 | Lowry et al. | |
| 2008/0077028 A1 | 3/2008 | Schaldach et al. | |
| 2008/0081962 A1 | 4/2008 | Miller et al. | |
| 2008/0082132 A1 | 4/2008 | Annest et al. | |
| 2008/0103548 A1 | 5/2008 | Fowler et al. | |
| 2008/0114417 A1 | 5/2008 | Leyde | |
| 2008/0119900 A1 | 5/2008 | DiLorenzo | |
| 2008/0125820 A1 | 5/2008 | Stahmann et al. | |
| 2008/0139870 A1 | 6/2008 | Gliner et al. | |
| 2008/0146890 A1 | 6/2008 | LeBoeuf et al. | |
| 2008/0146959 A1 | 6/2008 | Sheffield et al. | |
| 2008/0161712 A1 | 7/2008 | Leyde | |
| 2008/0161713 A1 | 7/2008 | Leyde et al. | |
| 2008/0161879 A1 | 7/2008 | Firlik et al. | |
| 2008/0161880 A1 | 7/2008 | Firlik et al. | |
| 2008/0161881 A1 | 7/2008 | Firlik et al. | |
| 2008/0161882 A1 | 7/2008 | Firlik et al. | |
| 2008/0183096 A1 | 7/2008 | Snyder et al. | |
| 2008/0183097 A1 | 7/2008 | Leyde et al. | |
| 2008/0183245 A1 | 7/2008 | Van Oort et al. | |
| 2008/0195175 A1 | 8/2008 | Balzer et al. | |
| 2008/0200925 A1 | 8/2008 | Johnson et al. | |
| 2008/0208013 A1 | 8/2008 | Zhang et al. | |
| 2008/0208074 A1 | 8/2008 | Snyder et al. | |
| 2008/0208285 A1 | 8/2008 | Fowler et al. | |
| 2008/0208291 A1 | 8/2008 | Leyde et al. | |
| 2008/0208781 A1 | 8/2008 | Snyder | |
| 2008/0215112 A1 | 9/2008 | Firlik et al. | |
| 2008/0215114 A1 | 9/2008 | Stuerzinger et al. | |
| 2008/0221644 A1 | 9/2008 | Vallapureddy et al. | |
| 2008/0234598 A1 | 9/2008 | Snyder et al. | |
| 2008/0249591 A1 | 10/2008 | Gaw et al. | |
| 2008/0255582 A1 | 10/2008 | Harris | |
| 2009/0054795 A1 | 2/2009 | Misczynski et al. | |
| 2009/0076567 A1 | 3/2009 | Fowler et al. | |

FOREIGN PATENT DOCUMENTS

| | | |
|---|---|---|
| EP | 0402683 A2 | 12/1990 |
| EP | 0713714 A2 | 5/1996 |
| EP | 1647300 A2 | 2/1998 |
| EP | 1070518 A2 | 1/2001 |
| EP | 1120130 A2 | 1/2001 |
| EP | 1145736 A2 | 10/2001 |
| EP | 1595497 A1 | 5/2004 |
| EP | 1486232 A2 | 12/2004 |
| GB | 2026870 A | 2/1980 |
| GB | 2079610 A | 1/1982 |
| WO | 9302744 A1 | 8/1992 |
| WO | 9417771 A2 | 2/1998 |
| WO | 9825688 A1 | 6/1998 |
| WO | 0040143 A1 | 12/1999 |
| WO | 0064336 A1 | 11/2000 |
| WO | 0105467 A1 | 1/2001 |
| WO | 0108749 A1 | 2/2001 |
| WO | 0064336 C2 | 6/2002 |
| WO | 03076010 A1 | 9/2003 |
| WO | 03085546 A1 | 10/2003 |
| WO | 2004036377 A2 | 4/2004 |
| WO | 2004064918 A1 | 8/2004 |
| WO | 2004071575 A1 | 8/2004 |
| WO | WO2004064918 * | 8/2004 |
| WO | 2004075982 A1 | 9/2004 |
| WO | 2004112894 A1 | 12/2004 |
| WO | 2005007120 A2 | 1/2005 |
| WO | 2005007232 A2 | 1/2005 |
| WO | 2005028026 A1 | 3/2005 |
| WO | 2005053788 A1 | 6/2005 |
| WO | 2005067599 A2 | 7/2005 |
| WO | 2004069330 A1 | 8/2005 |
| WO | 2005101282 A2 | 10/2005 |
| WO | WO2005110215 A2 * | 11/2005 |
| WO | 2006014760 A1 | 2/2006 |
| WO | 2006019822 A2 | 2/2006 |
| WO | 2006050144 A1 | 5/2006 |
| WO | 2006122148 A2 | 11/2006 |
| WO | 2007066343 A2 | 6/2007 |
| WO | 2007072425 A2 | 6/2007 |
| WO | 2007124126 A2 | 11/2007 |
| WO | 2007124190 A2 | 11/2007 |
| WO | 2007124192 A1 | 11/2007 |
| WO | 2007142523 A1 | 12/2007 |

OTHER PUBLICATIONS

Bachman, D.,S. et al.; "Effects of Vagal Volleys and Serotonin on Units of Cingulate Cortex in Monkeys;" Brain Research , vol. 130 (1977). pp. 253-269.

Terry et al.; "The Implantable Neurocybernetic Prosthesis System", Pacing and Clinical Electrophysiology, vol. 14, No. 1 (Jan. 1991), pp. 86-93.

Bohning, D.E., et al.; "Feasibility of Vagus Nerve Stimulation—Synchronized Blood Oxygenation Level-Dependent Functional MRI;" A Journal of Clinical and Laboratory Research: Investigative Radiology; vol. 36, No. 8 (Aug. 2001); pp. 470-479.

Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.

Clark, K.B., et al.; "Posttraining Electrical Stimulation of Vagal Afferents with Concomitant Vagal Efferent Inactivation Enhances Memory Storage Processes in the Rat" Neurobiology of Learning and Memory, vol. 70, 364-373 (1998) Art. No. NL983863.

Clark, K.B., et al.; "Enhanced Recognition Memory Following Vagus Nerve Stimulation in Human Subjects;" Nature Neuroscience, vol. 2, No. 1, (Jan. 1999) pp. 93-98.

DeGiorgo, Christopher M., et al.; "Vagus Nerve Stimulation: Analysis of Device Parameters in 154 Patients During the Long-Term XE5 Study;" Epilepsia, vol. 42, No. 8; pp. 1017-1020 (2001).

Devous, Michael D., et al.; "Effects of Vagus Nerve Stimulation on Regional Cerebral Blood Flow in Treatment-Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Dodrill, Ph.D., et al.; "Effects of Vagal Nerve Stimulation on Cognition and Quality of Life in Epilepsy;" Epilepsy and Behavior, vol. 2 (2001); pp. 46-53.

Fanselow, E. E., et al.; "Reduction of Pentylenetetrazole-Induced Seizure Activity in Awake Rats by Seizure-Triggered Trigeminal Nerve Stimulation;" The Journal of Neuroscience, vol. 20, No. 21; (Nov. 2000); pp. 8160-8168.

George, M.S., et al.; "Open Trial of VNS Therapy in Severe Anxiety Disorders;" 156th American Psychiatric Association Annual Meeting; May 17-22, 2003.

George, M.S., et al.; "Vagus Nerve Stimulation: A New Tool for Brain Research and Therapy;" Society of Biological Psychiatry vol. 47 (2000) pp. 287-295.

Hallowitz, R.A., et al.; "Effects of Vagal Volleys on Units of Intralaminar and Juxtalaminar Thalamic Nuclei in Monkeys;" Brain Research, vol. 130 (1977), pp. 271-286.

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychiatry, (May, 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Liebman, K.M. et al., "Improvement in Cognitive Function After Vagal Nerve Stimulator Implantation;" Epilepsia, vol. 39, Suppl. 6 (1998) 1 page.

Malow, B.A., et al.; "Vagus Nerve Stimulation Reduces Daytime Sleepiness in Epilepsy Patients" Neurology 57 (2001) pp. 879-884.

McClintock, P., "Can Noise Actually Boost Brain Power" Physics World Jul. 2002; pp. 20-21.

Mori, T., et al.; "Noise-Induced Entrainment and Stochastic Resonance in Human Brain Waves" Physical Review Letters vol. 88, No. 21 (May 2002); pp. 218101-1-218101-4.

Rugg-Gunn, F.J., et al.; "Cardiac Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents;" IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation;" Epilepsia, vol. 39, No. 7 (1998) pp. 677-686.

Tatum, W.O., et al.; "Ventricular Asystole During Vagus Nerve Stimulation for Epilepsy in Humans" American Academy of Neurologgy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdes-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck et al. "The Mechanism of Action of Vagus Nerve Stimulation for Refractory Epilepsy", Journal of Clinical Neurophysiology, vol. 18(5) (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Zabara, J. "Inhibition of Experimental Seizures in Canines by Repetivie Vagal Stimulation" Epilepsia vol. 33, No. 6 (1992); pp. 1005-1012.

Fromes, G., et al.; "Clinical Utility of On-Demand Magnet Use with Vagus Nerve Stimulation;" AES Proceedings.

Craig, A.D. (BUD); "Distribution of Trigeminothalamic and Spinothalamic Lamina I Terminations in the Macaque Monkey;" The Journal of Comparative Neurology, vol. 477, pp. 119-148 (2004).

Harry, J.D., et al.; "Balancing Act: Noise is the Key to Restoring the Body's Sense of Equilibrium;" IEEE Spectrum (Apr. 2005)pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" Epilepsia vol. 39, No. 9; pp. 984-990 (1998).

Woodbury, et al., "Vagal Stimulation Reduces the Severity of Maximal Electroshock Seizures in Intact Rats. Use of a Cuff Electrode for Stimulating and Recording"; Pacing and Clinical Electrophysiology, vol. 14 (Jan. 1991), pp. 94-107.

\* cited by examiner

COMPENSATION REDUCTION IN TISSUE STIMULATION THERAPY

BACKGROUND

1. Technical Field

The subject matter of this disclosure generally relates to the field of implantable medical devices. More specifically, the present disclosure relates to reducing compensation in tissue stimulation therapy, and particularly electrical neurostimulation therapy.

2. Background Information

Implantable medical devices (IMDs) are used to treat a variety of diseases and disorders. Some types of IMDs apply an electrical signal to a patient's body tissue to which the IMD is coupled. For example, a neurostimulator can be coupled to a patient's vagus nerve to provide an electrical signal to the nerve to treat seizure disorders such as epilepsy. Providing an electrical signal to the vagus nerve can also be therapeutically beneficial to treat other conditions, including depression and various eating disorders such as bulimia nervosa.

The body is known to compensate or alter its response to repeated stimuli. For example, after receiving an electrical neurostimulation therapy over an extended period of time, the body may adapt or compensate in response to the repeated application of the electrical signal, thereby rendering the therapy provided by the IMD less beneficial. When this happens, a healthcare provider may adjust the operation of the IMD. An IMD adjustment may involve altering one or more operating parameters that define the electrical signal, such as current amplitude, pulse width, pulse frequency, on time, off time, etc. After the adjustment has been made to the electrical parameter(s), the body eventually may again compensate to the therapy provided by the IMD, thereby again rendering the therapy provided by the IMD less beneficial. Numerous adjustments may thus be required because the body may continually compensate to the therapy. Each IMD adjustment usually requires a visit to the physician that, for many patients, is time-consuming, expensive, and generally undesirable.

BRIEF SUMMARY

The present disclosure addresses the issues noted above by reducing or preventing the body from compensating to a given therapy protocol delivered by an implanted medical device. The disclosed techniques involve a change from a first therapy protocol to a second therapy protocol based on the occurrence of an event (e.g., an elapsed time interval, user activations of the therapy, input from a physiological sensor, etc.). The first and second therapy protocols differ in terms of the on-time and off-time, but effectuate the same or a similar duty cycle. Therapy protocols that have the same duty cycle, albeit with different settings for on-time and off-time, may result in similar therapeutic benefits to the patient. The implanted medical device preferably switches from the first such therapy protocol to the second before the body has a chance to compensate for the first therapy protocol.

In at least one embodiment, a method comprises delivering an electrical signal to a nerve according to a first setting of an on-time and off-time that defines a duty cycle. The method also comprises automatically changing the first setting to a second setting of on-time and off-time in response to an event. The second setting defines a duty cycle substantially equal to the duty cycle defined by the first setting.

In another embodiment, a system comprises a pulse generator that provides an electrical signal to a nerve and a controller coupled to the pulse generator. The controller causes the pulse generator to deliver an electrical signal to a nerve according to a first setting of an on-time and off-time that defines a duty cycle. In response to a first event, the controller also causes a change from the first setting to a second setting of an on-time and off-time that defines the same or similar duty cycle as defined by the first setting.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
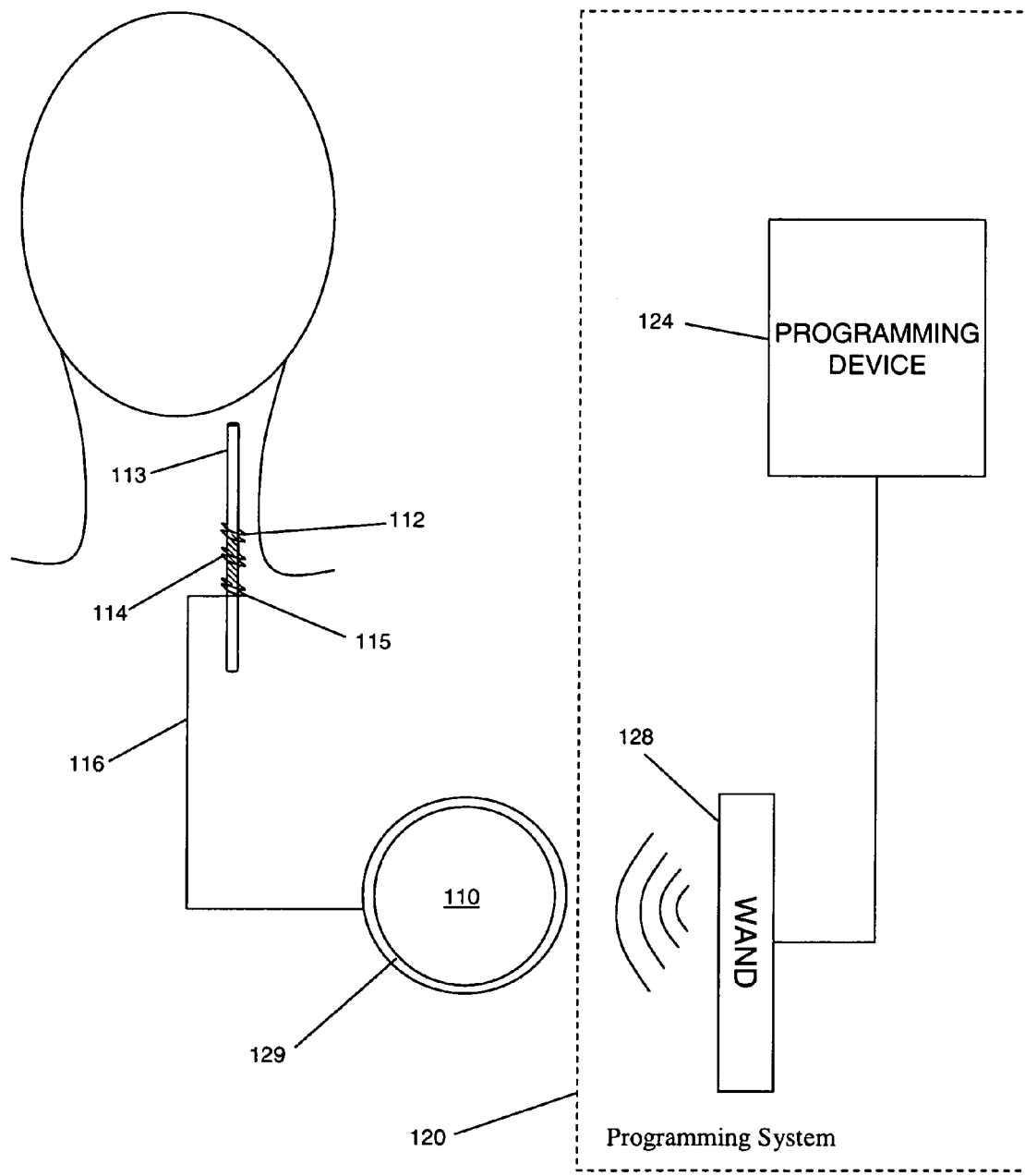
FIG. 1 depicts, in schematic form, an implantable medical device, in accordance with a preferred embodiment of the invention, implanted within a patient and programmable by an external programming system.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections. The terms "substantially the same as" and "substantially equal to," when used in conjunction with an electrical signal parameter such as duty cycle, refer to two parameters differing by no more than 25%, preferably no more than 10%, and more preferably by no more than 5%.

DETAILED DESCRIPTION OF THE PREFERRED EMBODIMENTS

The present invention is susceptible to implementation in various embodiments. The disclosure of specific embodiments, including preferred embodiments, is not intended to limit the scope of the invention as claimed unless expressly specified. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

The following description is presented largely in terms of vagus nerve stimulation ("VNS"). However, the disclosure and claims that follow are not limited to VNS, and may be applied to the delivery of an electrical signal to modulate the electrical activity of other cranial nerves such as the trigeminal and/or glossopharyngeal nerves, or to other neural tissue such as one or more brain structures of the patient, spinal nerves, and other spinal structures. Further still, other embodiments of the invention can be implemented to stimulate tissue other than nerves or neural tissue, such as cardiac tissue, muscle tissue, connective tissue, or bone tissue.

As discussed above, it is known that the body compensates or alters its response in reaction to repeated electrical signals applied to a target tissue. In the case of neurostimulation therapy applied to a nerve, without being bound by theory the body may adapt by changes to the nerve itself (which may include structural and/or functional changes), changes in one or more brain centers involved in processing electrical signals from the nerve, or both. In addressing the problem of compensation or adaptation, various embodiments of the invention comprise an implantable medical device (IMD) that alters its therapy protocol to reduce or prevent the body from compensating to the therapy. The therapy protocol provided by the IMD comprises an electrical signal applied to a target tissue, with the signal characterized by a set of parameters. The parameters comprise, in at least some embodiments, pulse frequency, pulse width, current amplitude, on-time, and off-time. One therapy protocol differs from another therapy based on differences in the underlying parameters that define each therapy protocol. The "on-time" refers to the time period during which the IMD is actively stimulating tissue and the "off-time" refers to the time period in which no stimulation is provided.

Figure 4:
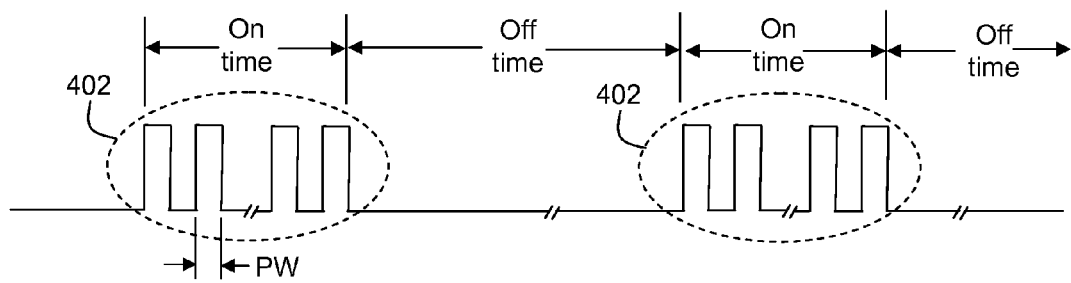
FIG. 4 provides an illustrative waveform showing on-time and off-time.
Figure 4A:
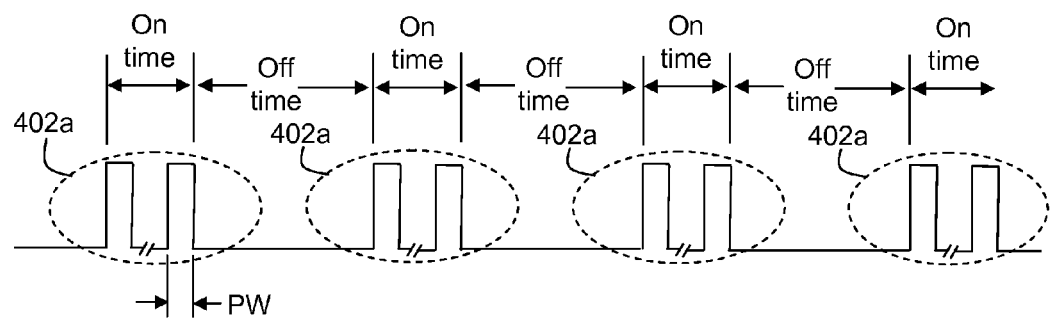

FIG. 4A provides another illustrative waveform showing on-time and off-time but with the same or similar duty cycle to that of FIG. 4.

In general, the IMD described herein provides a therapy protocol in which a therapy signal (which may comprise an electrical signal, a mechanical signal such as a vibration signal, an optical signal, a chemical signal, or another type of signal) is provided to the target tissue for an on-time and then turned off (i.e., not provided to the target tissue) during an off-time. The therapy protocol then typically repeats itself over and over until the IMD is reprogrammed, or another intervention occurs, such as a manual intervention by the patient to temporarily deliver a different protocol for a short time period.

Referring to FIG. 4, in electrical neurostimulation therapy such as vagus nerve stimulation therapy, the electrical signal is typically applied to the nerve as a pulsed electrical signal that is defined by a plurality of parameters. These may include current amplitude, pulse width (PW), and pulse frequency. The electrical signal as thus defined is typically applied to the nerve in a series of pulses known as a burst 402. The burst is defined by an on-time, e.g., 30 seconds. For pulsed electrical signals, the on-time includes interpulse periods in which no electrical pulse is being applied to the nerve. The on-time period is followed by an off-time period in which no signal is applied to the nerve. The therapy is provided by cycling between on-time and off-time periods.

The "duty" cycle of such a therapy protocol is the percentage of time in which the signal is being provided to the target tissue, i.e., it is the ratio of on-time to the sum of on-time and off-time. For example, a 50% duty cycle means that the on-time is equal to the off-time, and the electrical signal is being provided half of the time. It is important to note that where the signal is a pulsed signal, an electrical pulse is actually applied to the nerve for a small fraction of the total on-time. For example, in a 30 second burst (i.e., 30 second on-time) having a frequency of 20 Hz and a pulse width of 0.5 milliseconds, electrical charge is actually being delivered to the nerve for only 10 milliseconds (20 Hz×0.5 milliseconds) each second of the burst, or 1% of the on-time. However, the entire 30 second on-time period is included in calculating the duty cycle. Thus, for pulsed electrical signals duty cycle is not the percentage of time that electrical charge is being delivered to the nerve, but the percentage of on-time to total time. In the alternative embodiment of non-pulsed signals, on the other hand, the duty cycle may equal the percentage of time that charge is delivered to the nerve.

As discussed above, it is known that a nerve compensates or alters its response in reaction to repeated stimulation therapy. In addressing this problem, various embodiments of the invention comprise an implantable medical device (IMD) that alters its therapy protocol to reduce or prevent compensation. The therapy protocol provided by the IMD comprises an electrical stimulation characterized by a set of parameters. Such parameters comprise, in at least some embodiments, frequency, pulse width, current amplitude, on-time, and off-time. One therapy protocol differs from another therapy based on the underlying parameters. The "on-time" refers to the time period during which the IMD is actively stimulating tissue and the "off-time" refers to the time period in which no stimulation is provided. FIG. 4A, for example, illustrates different settings of on-time of pulse bursts 402a and off-time compared to FIG. 4, but has the same or substantially the same duty cycle to that of FIG. 4.

In accordance with some embodiments of the invention, the IMD automatically changes the on-time and off-time parameter settings periodically, without appreciably changing the duty cycle. It has been discovered that two or more therapy protocols having different on-time and off-time settings, while all other parameters remain substantially the same, including in particular duty cycle, may provide the same or similar therapeutic benefit to the patent while avoiding compensation for the signal that may reduce therapeutic benefit to the patient. Thus, in accordance with at least some embodiments, the IMD automatically changes the settings of on-time and off-time, while maintaining the duty cycle largely the same. Doing so reduces or avoids the body's tendency to compensate to the therapy protocol being delivered. That is, the body does not have a chance to compensate before the IMD changes the therapy protocol to a different therapy protocol with the same or a similar duty cycle. It has been discovered that where the duty cycle remains largely the same, the therapeutic efficacy to the patient likewise remains largely the same from one therapy to the next, but the tendency to compensate is reduced or eliminated. It is believed that such a periodically changing protocol may enable certain patients who would otherwise adapt to the therapy (thereby reducing or eliminating a therapeutic benefit) to instead maintain therapeutic efficacy.

FIG. 1 illustrates an implantable medical device ("IMD") 110 implanted in a patient. The IMD 110 may be representative of any of a variety of medical devices that provide a signal (e.g., an electrical, mechanical, chemical, or optical signal) to a target tissue of a patient. At least one preferred embodiment of the IMD 110 comprises a neurostimulator for applying an electrical signal to a neural structure in a patient, particularly a cranial nerve such as a vagus nerve 113. A lead assembly 116 is coupled to the IMD 110 and includes one or more electrodes, such as electrodes 112 and 114. Lead 116 has a proximal end that connects to the IMD 110 and a distal end on which the electrodes are provided. The outer housing (or "can") 129 of the IMD 110 preferably is electrically conductive and thus may also function as an electrode. The electrodes, such as electrodes 112, 114 and can 129, can be used to apply an exogenous electrical signal to and/or sense the electrical activity of the associated tissue (e.g., the vagus nerve 113). In one embodiment, a strain relief tether 115 comprises an attachment mechanism to help secure the lead assembly 116 to the nerve 113 and to provide strain relief. An example of a suitable strain relief tether is described in U.S. Pat. No. 4,979,511, incorporated herein by reference.

FIG. 1 also illustrates an external programming system 120 comprising a programming device 124 coupled to a wand 128. The programming device 124 may comprise a personal computer, handheld computer (e.g., a personal digital assistant (PDA) device), or other suitable computing device consistent with the description contained herein. Methods and apparatus for communication between the IMD 110 and an external programming system 120 are known in the art. As explained below, in one embodiment the IMD 110 includes a transceiver (such as a coil) that permits signals to be communicated wirelessly and non-invasively between the external wand 128 and the implanted IMD 110. Via the wand 128, the programming system 120 generally monitors the performance of the IMD 110 and downloads new programming parameters (e.g., on-time, off-time, pulse width, current amplitude, and pulse frequency) into the device to alter its operation as desired.

Figure 2:
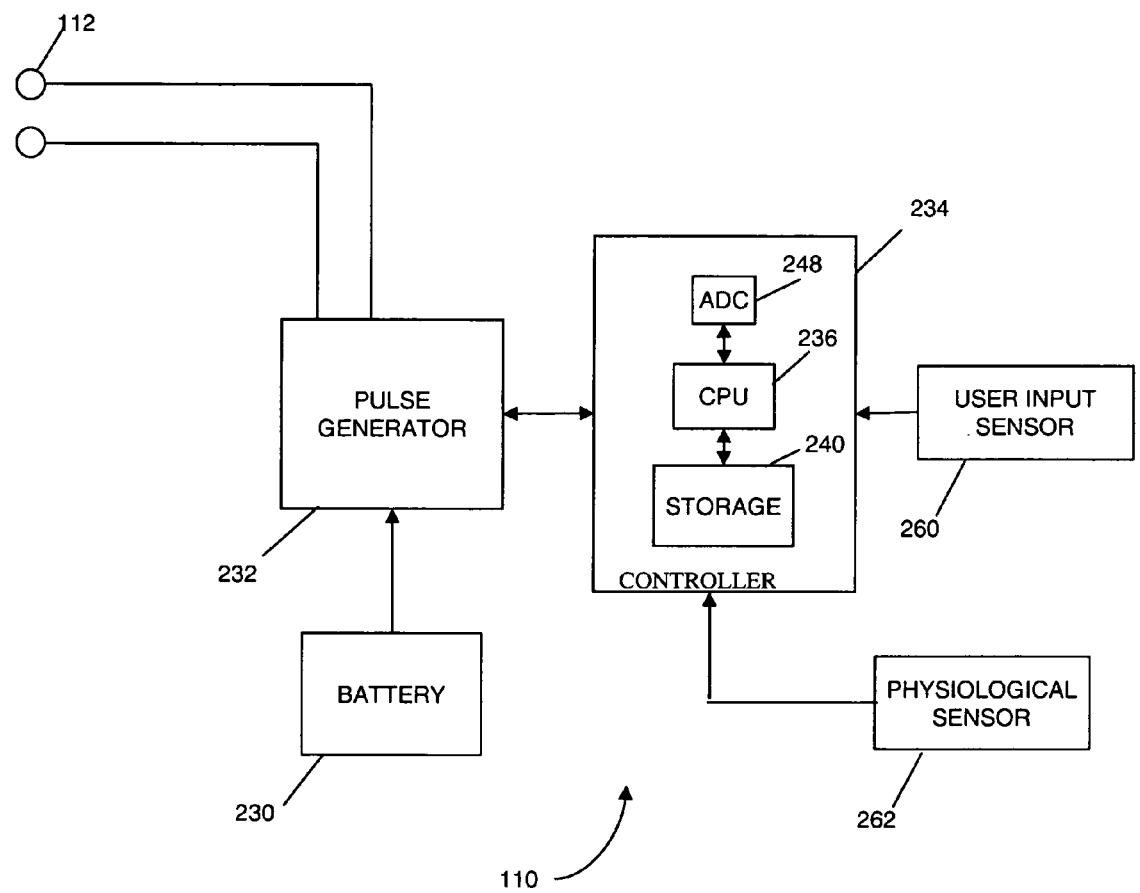
FIG. 2 is a block diagram of the implantable medical device of FIG. 1 and comprising a user input sense device.

FIG. 2 shows a block diagram of one embodiment of the IMD 110. As shown, the IMD 110 comprises a system that includes a battery 230, a pulse generator 232, and a controller 234. Under the control of controller 234, the pulse generator 232 generates an electrical signal to apply to a target tissue (e.g., a vagus nerve 113) in a patient. The battery 230 provides power to both the pulse generator 32 and, via the pulse generator, to the controller 234. The controller 234 generally assists, controls, and/or programs the pulse generator 232. Controller 234 preferably comprises a central processing unit (CPU) 236 such as a low-power, mixed-signal microcontroller. In general, any suitable processor can be used to implement some or all of the functionality explained herein.

The CPU 236 preferably couples to one or more analog-to-digital converters (ADCs) 48 and storage 240. The storage 240 preferably comprises volatile and/or non-volatile memory. The non-volatile memory may comprise Flash memory. The volatile memory may comprise any suitable type of random access memory (RAM). The storage 240 is used to store code that is executed by the CPU 236. Such executable code may be loaded into the IMD 110 during manufacturing and/or may be downloaded to the IMD from the programming system 120 after implantation. The executable code may be loaded into non-volatile memory and either executed directly from the non-volatile memory or copied to the volatile memory for execution therefrom.

The storage 240 or other storage (e.g., registers) in the pulse generator 232 may be used to store the parameter settings that define a therapy protocol or program. In accordance with a preferred embodiment of the invention, the IMD 110 may be programmed with a plurality of therapy protocols. The therapy protocols may be loaded into IMD 110 during manufacturing and/or downloaded to the IMD 110 from programming system 120 after implantation. The controller 234 can cause the pulse generator 232 to operate in accordance with any suitable therapy protocol from among one or more such protocols programmed into the IMD 110.

In a preferred embodiment, the IMD 110 includes a user input sensor 260 and a physiological sensor 262. Sensor 260 is used to sense an external user input such as a tap, a magnetic field, a sound, etc. Sensor 260 can be used to provide manual control of the IMD 110 by a person (e.g., the patient in which the IMD is implanted). The sensor 260 is preferably integrated within the IMD 110, but in alternative embodiments can be physically separate.

In at least one embodiment, user input sensor 260 comprises an implanted tap sensor such as an accelerometer. The tap sensor provides an electronic signal to the IMD 110 in response to a patients' physical tap or touching of the skin over the location of the implanted tap sensor. In another embodiment, the sensor 260 comprises a Reed switch that can be opened or closed by a magnet that is placed in close proximity to the IMD 110. In this embodiment, the patient may be provided with a magnet that when placed near the IMD provides a magnetic field as an input to the Reed switch, to thereby control one or more operations of the IMD 110.

Sensor 262 is sensitive to a physiological parameter of the patient in which the IMD 110 is implanted. Any number of such sensors may be included for sensing one or more physiological parameters of the patient's body functions. Physiological sensor(s) 262 may comprise any or all of the following non-limiting examples: electrodes that sense electrical activity, a pressure transducer, an acoustic element, a photonic element, a blood pH sensor, a blood pressure sensor, a blood sugar sensor, and a body movement sensor. Accordingly, the sensors 262 that are coupled to the IMD 110 are capable of sensing one or more physiological parameters selected from the following exemplary list: an action potential in a nerve tissue, a heart parameter, a body temperature, a blood parameter (e.g., pH, pressure), food intake, gastric (e.g., stomach and/or intestinal) function, and brain activity.

Figure 3:
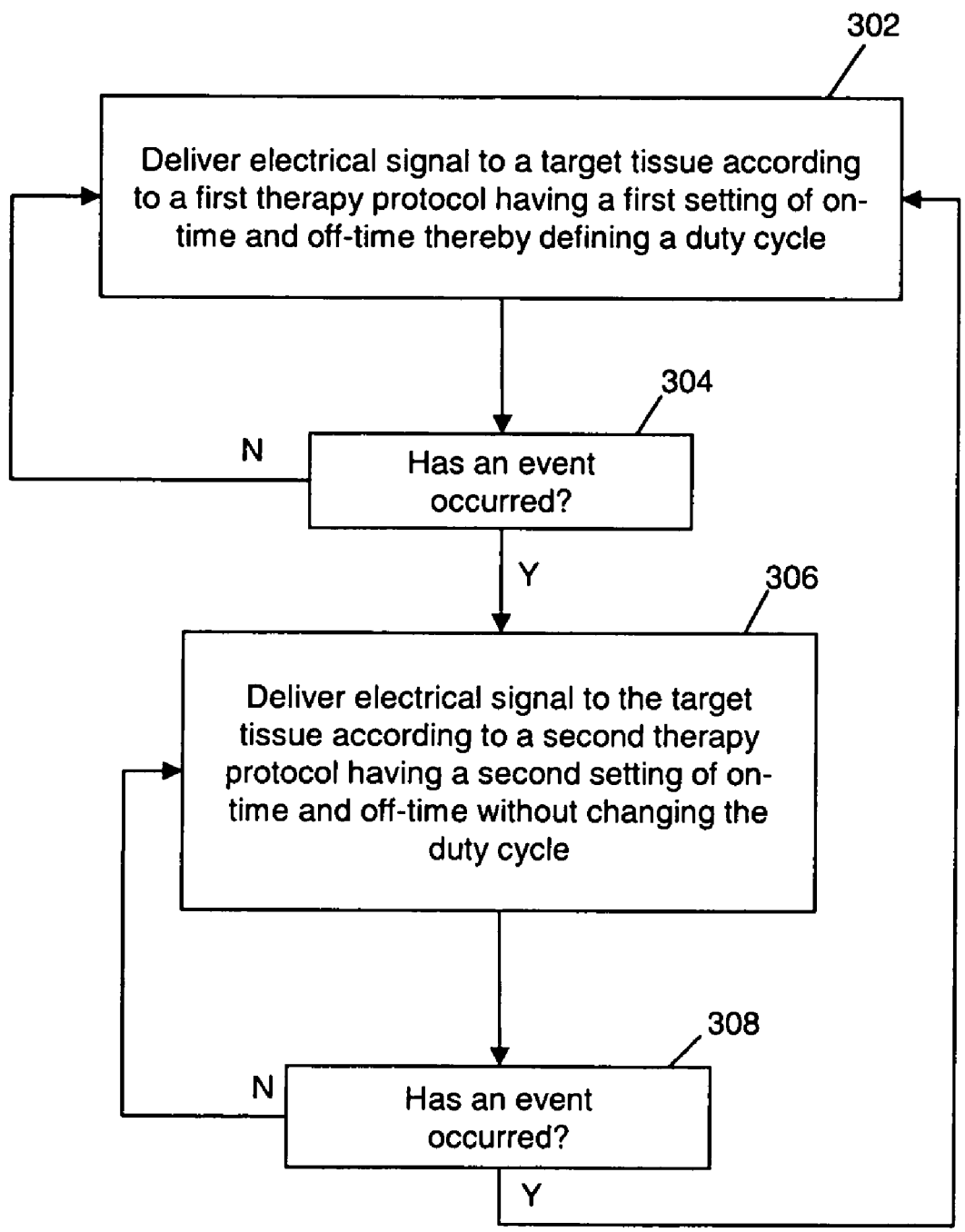
FIG. 3 illustrates a flow diagram of an embodiment of a method for treating or preventing compensation in tissue stimulation therapy.

FIG. 3 illustrates a method 300 for reducing compensation of the patient's body to a therapy protocol performed by an IMD. In block 302, an electrical signal is delivered to a target tissue (e.g., a vagus nerve) by the IMD 110 according to a first therapy protocol having a first setting of on-time and off-time which defines a particular duty cycle. In block 304, the IMD 110 determines the occurrence of an event. In at least some embodiments, the event in block 304 comprises the expiration of a time period associated with the first on-time/off-time setting. That time period can be any fixed or programmable period of time such as 1 hour, 1 day, 1 month, etc. In other embodiments, the event may comprise a user activation parameter that is manually provided by a user to the user input sensor 260, or a physiological event that may be automatically sensed by physiological sensor 262 (FIG. 2). Once the event is determined to have occurred in block 304, the IMD 110 at block 306 changes the first on-time/off-time setting to a second on-time/off-time setting while maintaining the same or a substantially similar duty cycle, and delivers to the target tissue an electrical signal according to a second therapy protocol employing the second on-time/off-time setting. As such, the therapy protocol changes in block 306 relative to the therapy protocol of block 302 but, with the duty cycle remaining the same, the therapeutic efficacy of the therapy protocol may be maintained or improved.

The IMD in block 308 again determines whether an event has occurred. The event in block 308 may comprise an event of the type referred to in regard to block 304, e.g., a time period associated with the second on-time/off-time setting or a physiological event sensed by physiological sensor 262. In one embodiment, the IMD 110 continues providing an electrical signal according to the second therapy protocol and the second on-time/off-time setting for a fixed or programmable period of time that may be the same as, or different from, a time period associated with the first on-time/off-time setting and the first therapy protocol. At the end of the time period for the second therapy protocol, control reverts back to block 302 at which the process repeats. Each setting for on-time and off-time may be computed based on a prior setting.

In the embodiment of FIG. 3, the IMD 110 thus provides an electrical signal to target tissue in alternating fashion in accordance with the first therapy protocol defined by a first on-time/off-time setting and then in accordance with the second therapy protocol defined by a second on-time/off-time setting. In other embodiments, more than two therapy protocols with the same or similar duty cycle can be implemented. For example, three therapy protocols can be implemented sequentially, each therapy being implemented for a specific period of time.

In accordance with some embodiments, the events occurring in blocks 304 and 308 may be other than time periods. In certain embodiments, the event may be indicated manually by a user via user input sensor 260. A user input such as a magnet may be used to signal any of a variety of user activation parameters, such as an indication of a binge/purge episode, a desire for therapy, or other parameters indicating an input from a user (e.g., the patient or a physician). In other embodiments, a physiological sensor 262 can be used to automatically detect one or more body parameters, changes of which in excess of a threshold value are the event. For example, the event may be physiological in nature such as, via a sensor 260 or 262, a bulimia patient binging and/or purging, either a single episode of binging and/or purging or binging and/or purging in excess of a predefined or programmable rate. Episodes of binging and/or purging can be detected by a variety of methods, including a manual indication by the patient or automatic detection of a body parameter such as swallowing, automatically detected gastric motility motion (e.g., stomach contractions), blood parameters such as a rapid increase in blood sugar or insulin secretion (which may be indicated either automatically via physiological sensor 262 or manually via user input sensor 260 after a conventional blood glucose test), sensed vagus nerve electrical activity, and other physiologically sensed body parameters. In some embodiments, the events in blocks 304, 308 comprise the determination that the patient has communicated (e.g., via tapping, a magnet, etc.) with a user input sensor 260 more than a threshold number of times in a given period of time. For example, a bulimia patient can manually activate the sensor 260 each time the patient feels a desire to binge or purge. If the rate at which the patient feels a need to binge and/or purge exceeds a specified rate, the IMD 110 will automatically switch to the next scheduled therapy protocol.

In some embodiments as explained above, switching from one therapy protocol to the next can be based on time, based on a rate at which the user activates sensor 260, or based on a detection of physiological events (e.g., binging/purging). Further still, switching from one therapy protocol to the next can occur based on one or more of the expiration of defined time periods for each therapy protocol, manual activation of user input sensor 260, and/or detection of a physiological event. For example, the IMD 110 switches from one therapy protocol to another at defined time intervals, but one therapy protocol can be terminated prematurely in favor of the next scheduled therapy protocol if the user activates the sensor device 260 at a rate greater than a threshold rate.

In accordance with at least some embodiments, user input sensor 260 can also be used by a person (e.g., the patient in which the IMD 110 is implanted) to provide additional information to the IMD 110. In some embodiments, the IMD's controller 234 determines an action to be performed according to the number of user activations of the user input sensor 260. For example, a patient may activate the user input sensor device 260 once to signify the occurrence of a physiological or psychological event (e.g., the desire to binge or purge). The IMD 110 may then record in, for example, storage 240 that such an event has occurred. Such information can be used for a variety of purposes such as verifying the accuracy of what a bulimic patient reports to a healthcare provider regarding his or her desire to binge and purge.

In at least some embodiments, user activations of the user input sensor 260 can be performed to cause the IMD 110 to deliver an immediate stimulation. The number of user activations may encode the type of stimulation to be delivered. For example, three activations of sensor 260 in quick succession may cause the IMD 110 to deliver a larger stimulation level (e.g., greater current amplitude) than two activations of sensor 260 in quick succession.

Although the present invention and its advantages have been described in detail, it should be understood that various changes, substitutions and alterations may be made herein without departing from the spirit and scope of the invention as defined by the appended claims.

What is claimed is:

1. A method of treating a patient, comprising:
    delivering an electrical signal to a nerve according to a first setting of an on-time and off-time that defines a duty cycle, wherein said on-time defines the time during which an electrical burst of pluses occurs and said off-time defines the time with no electrical burst of pulses; and
    automatically changing said first setting to a second setting of on-time and off-time in response to a physiological event, wherein said second setting defines a duty cycle substantially equal to the duty cycle defined by said first setting;
    wherein said second setting is different from said first setting.

2. The method of claim 1, wherein changing said first setting to the second setting further comprises sensing an occurrence of said physiological event followed by changing said first setting to said second setting and repeating said sensing and changing.

3. The method of claim 1 wherein said physiological event comprises a change in a physiological parameter exceeding a defined threshold.

4. The method of claim 1, further comprising changing said first setting to the second setting upon detecting a sensed user input.

5. The method of claim 1, further comprising automatically changing said second setting to a third setting of on-time and off-time in response to a second event, wherein said third setting defines a duty cycle substantially equal to the duty cycle defined by said first and second settings.

6. A system, comprising:
    at least one electrode coupled to a nerve;
    a pulse generator coupled to said at least one electrode, wherein said pulse generator provides an electrical signal to a nerve using said at least one electrode; and a controller coupled to said pulse generator, wherein said controller causes said pulse generator to deliver said electrical signal to a nerve according to a first setting of an on-time and off-time that defines a first duty cycle and, in response to a physiological event, causes a change from said first setting to a second setting of an on-time and off-time that defines a second duty cycle that is no more than 5% different from the first duty cycle;

wherein said on-time defines the time during which an electrical burst of pulses occurs and said off-time defines the time with no electrical burst of pulses;

wherein said second setting is different from said first setting.

7. The system of claim 6, further comprising a user input sensor coupled to the controller, wherein said user input sensor senses a manual control input to control an operation of the pulse generator.

8. The system of claim 7, wherein said physiological event comprises a user activation parameter of said sensor in excess of an activation parameter threshold.

9. The system of claim 6, further comprising a physiological sensor coupled to the controller to control, at least in part, changing from the first setting to the second setting.

10. The system of claim 6 wherein said physiological event comprises a change in a physiological parameter exceeding a threshold.

11. The system of claim 10 further comprising a user input sensor capable of sensing a user input signal, and wherein said controller causes the change from said first setting to the second setting upon detection of the physiological event and upon at least one of an expiration of a defined time period and a sensed user input signal.

12. A method of treating a patient having a medical condition, comprising:

applying to a vagus nerve of the patient a first electrical signal defined by a first plurality of parameters comprising a first on-time and a first off-time defining a first duty cycle;

determining the occurrence of a physiological event and, in response to said physiological event ceasing said step of applying said first electrical signal to said vagus nerve, and applying to said vagus nerve a second electrical signal defined by a second plurality of parameters comprising a second on-time and a second off-time defining a second duty cycle that differs from said first duty cycle by no more than 10%;

wherein each of said first and second on=times defines a time during which an electrical burst of pulses occurs and each of said first and second off-times define a time with no electrical burst of pulses;

wherein said second electrical signal is different from said first electrical signal.

13. The method of claim 12 wherein said first plurality of parameters comprises at least one of a first current magnitude, a first frequency, and a first pulse width, and said second plurality of parameters comprises at least one of a second current magnitude, a second frequency, and a second pulse width.

14. The method of claim 13 wherein at least one of said second current magnitude, said second frequency, and said second pulse width is the same as a respective one of said first current magnitude, said first frequency, and said first pulse width.

15. The method of claim 12 wherein applying said second electrical signal is also in response to at least one of a defined time period or a sensed user input, in addition to physiological event.

16. The method of claim 12 further comprising:

detecting the occurrence of a second event, and in response to said second event ceasing said step of applying said second electrical signal to said vagus nerve, and applying said first electrical signal to said vagus nerve.

17. The method of claim 12 further comprising:

detecting the occurrence of a second event, and in response to said second event ceasing said step of applying said second electrical signal to said vagus nerve, and applying to said vagus nerve a third electrical signal defined by a third plurality of parameters comprising a third on-time and a third off-time characterized by a third duty cycle substantially the same as said first duty cycle.

18. The method of claim 12, wherein said second duty cycle differs from said first duty cycle by no more than 5%.

* * * * *